(12) United States Patent
Yamada et al.

(10) Patent No.: US 10,234,675 B2
(45) Date of Patent: *Mar. 19, 2019

(54) STEREOSCOPIC IMAGING APPARATUS

(71) Applicant: Sony Corporation, Tokyo (JP)

(72) Inventors: Masahiro Yamada, Kanagawa (JP); Sunao Aoki, Kanagawa (JP)

(73) Assignee: Sony Corporation, Tokyo (JP)

(*) Notice: Subject to any disclaimer, the term of this patent is extended or adjusted under 35 U.S.C. 154(b) by 75 days.

This patent is subject to a terminal disclaimer.

(21) Appl. No.: 14/796,176

(22) Filed: Jul. 10, 2015

(65) Prior Publication Data

US 2015/0316759 A1    Nov. 5, 2015

Related U.S. Application Data

(63) Continuation of application No. 13/287,712, filed on Nov. 2, 2011, now Pat. No. 9,110,367.

(30) Foreign Application Priority Data

Nov. 10, 2010    (JP) .................................. 2010-251750

(51) Int. Cl.
 *H04N 13/02* (2006.01)
 *G02B 23/24* (2006.01)
 (Continued)

(52) U.S. Cl.
 CPC ......... *G02B 23/2415* (2013.01); *G02B 21/22* (2013.01); *G02B 27/2214* (2013.01);
 (Continued)

(58) Field of Classification Search
 CPC .... G02B 27/2214; G02B 21/22; G02B 21/20; G02B 23/2415; H04N 13/0203; H04N 13/0242
 (Continued)

(56) References Cited

U.S. PATENT DOCUMENTS 4,640,586 A    2/1987  Iba et al.
5,689,365 A    11/1997  Takahashi
(Continued)

FOREIGN PATENT DOCUMENTS

CN    1176403 A    3/1998
CN    1278075 A    12/2000
(Continued)

OTHER PUBLICATIONS

Extended European Search Report dated Mar. 16, 2018 in connection with European Application No. 17174496.4.

*Primary Examiner* — Audrey Y Chang
(74) *Attorney, Agent, or Firm* — Wolf, Greenfield & Sacks, P.C.

(57) ABSTRACT

A stereoscopic imaging apparatus includes: an objective optical system having a function of imaging a subject as a real image or a virtual image; and plural imaging optical systems that image plural subject luminous fluxes output from different paths of the objective optical system again as parallax images using plural independent optical systems, wherein, in the case where a focal length value when the objective optical system images the subject as the real image is positive and the focal length value when the objective optical system images the subject as the virtual image is negative, a focal distance (f) of the objective optical system and a distance (L) from a rear principal point of the objective optical system to a front principal point of the imaging optical system is set to values that satisfy the following equation $$|f(L-f)| \leq 1.$$

17 Claims, 15 Drawing Sheets

(51) Int. Cl.
  *G02B 21/22* (2006.01)
  *G03B 35/10* (2006.01)
  *G02B 27/22* (2018.01)
  *G03B 35/08* (2006.01)
  *A61B 1/00* (2006.01)

(52) U.S. Cl.
  CPC ............ *G03B 35/08* (2013.01); *G03B 35/10* (2013.01); *A61B 1/00188* (2013.01); *A61B 1/00193* (2013.01)

(58) Field of Classification Search
  USPC ................ 359/375, 376, 377; 348/45, 49
  See application file for complete search history.

(56) References Cited

U.S. PATENT DOCUMENTS

| | | | | |
|---|---|---|---|---|
| 5,861,987 | A | * | 1/1999 | Nakamura ......... G02B 23/2415 359/429 |
| RE36,299 | E | | 9/1999 | Tanaka et al. |
| 6,157,495 | A | | 12/2000 | Kawasaki |
| 7,364,297 | B2 | | 4/2008 | Goldfain et al. |
| 7,602,555 | B2 | | 10/2009 | Kawasaki et al. |
| 9,110,367 | B2 | * | 8/2015 | Yamada ............. G02B 27/2214 |
| 2010/0238272 | A1 | | 9/2010 | Cameron et al. |
| 2010/0259600 | A1 | * | 10/2010 | Yoshikawa ............ G03B 35/08 348/49 |
| 2012/0113509 | A1 | | 5/2012 | Yamada et al. |

FOREIGN PATENT DOCUMENTS

| | | | | |
|---|---|---|---|---|
| DE | 195 32 400 A1 | | 3/1996 | |
| EP | 0134870 | | 9/1983 | |
| EP | 0134870 | | 3/1985 | |
| JP | 08-050258 | | 2/1996 | |
| JP | 2003-5313 | * | 1/2003 | ............... G02B 7/28 |
| JP | 2003-005313 | | 1/2003 | |
| JP | 2005-241791 | | 9/2005 | |
| WO | WO 92/19008 A1 | | 10/1992 | |

* cited by examiner

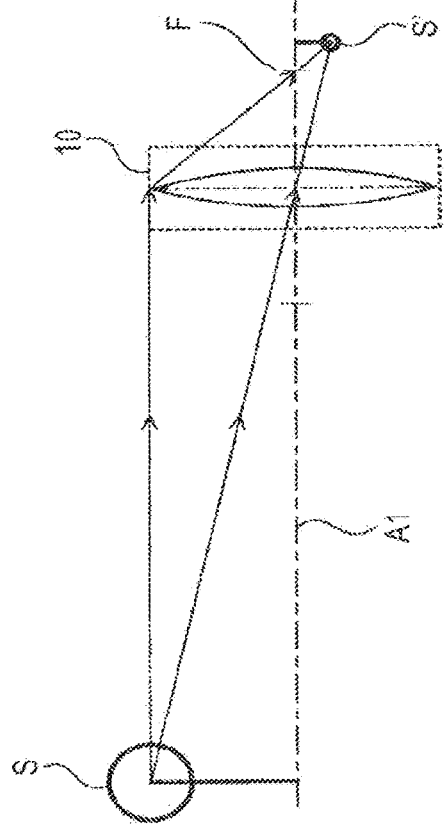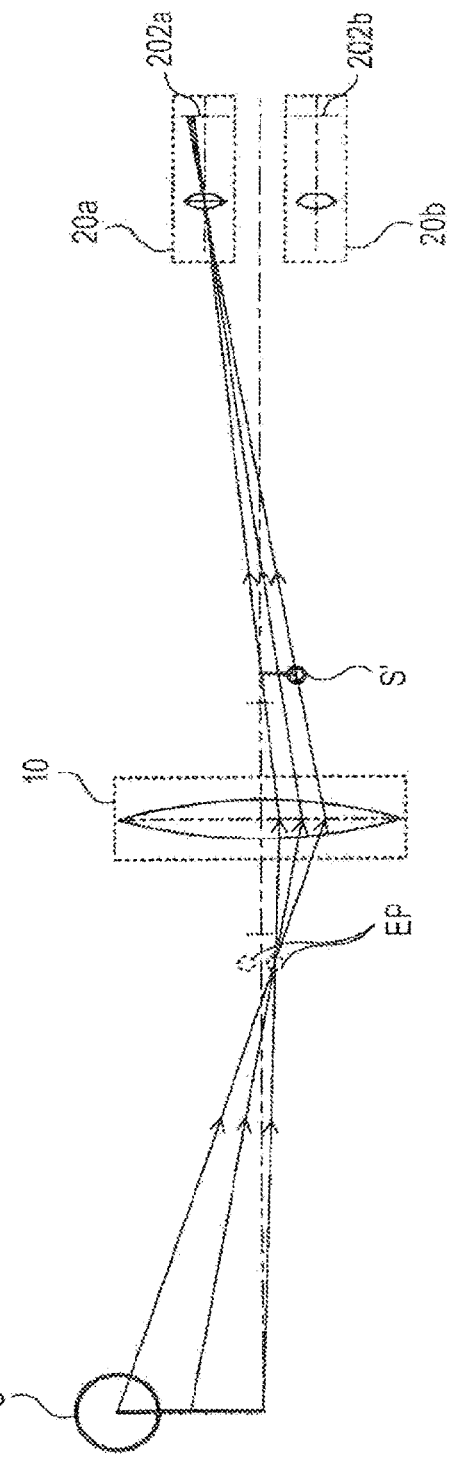

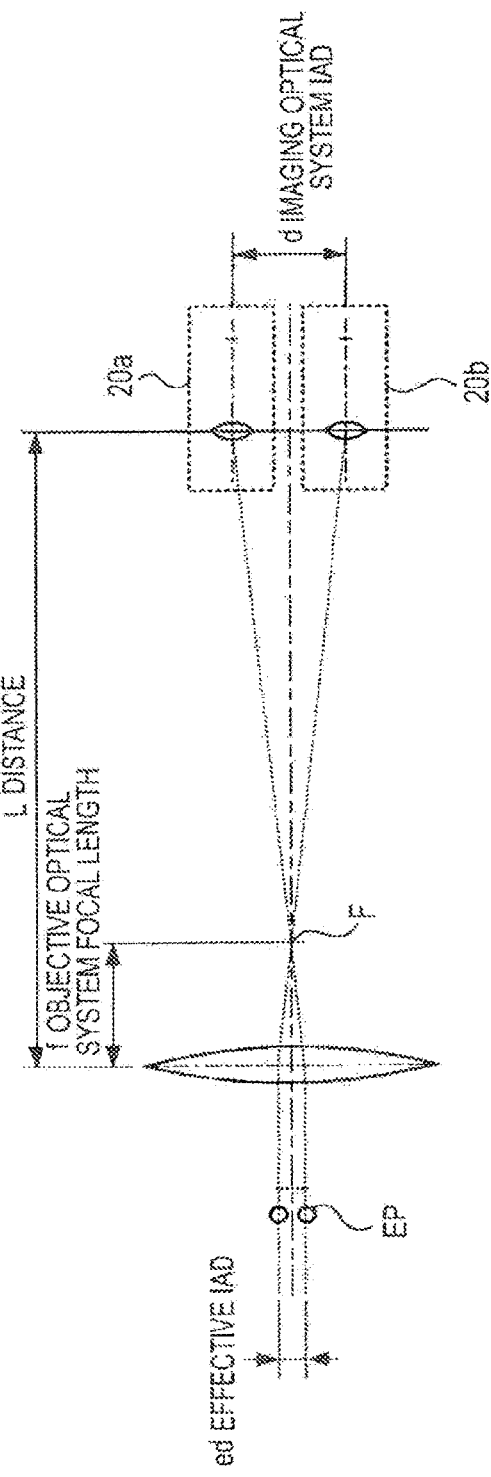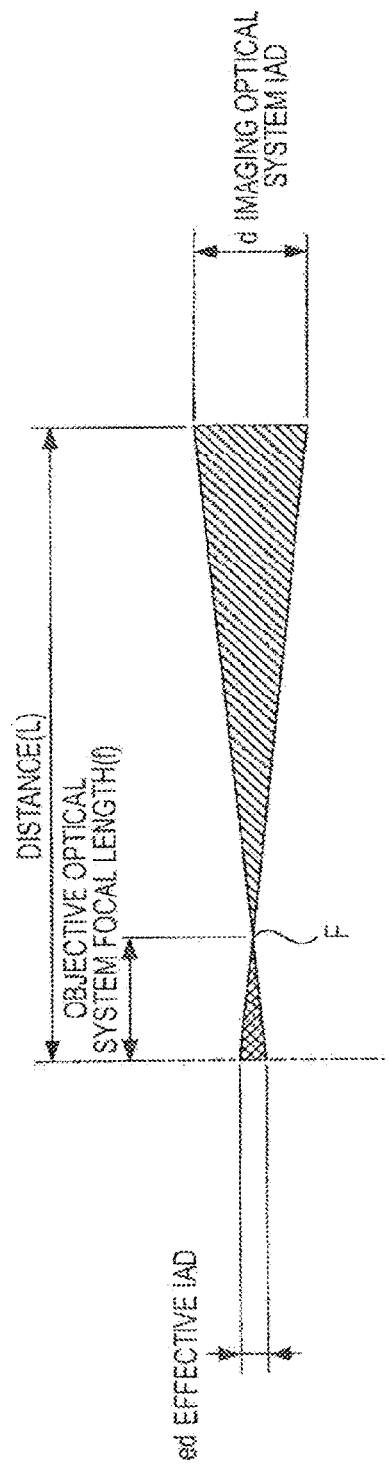

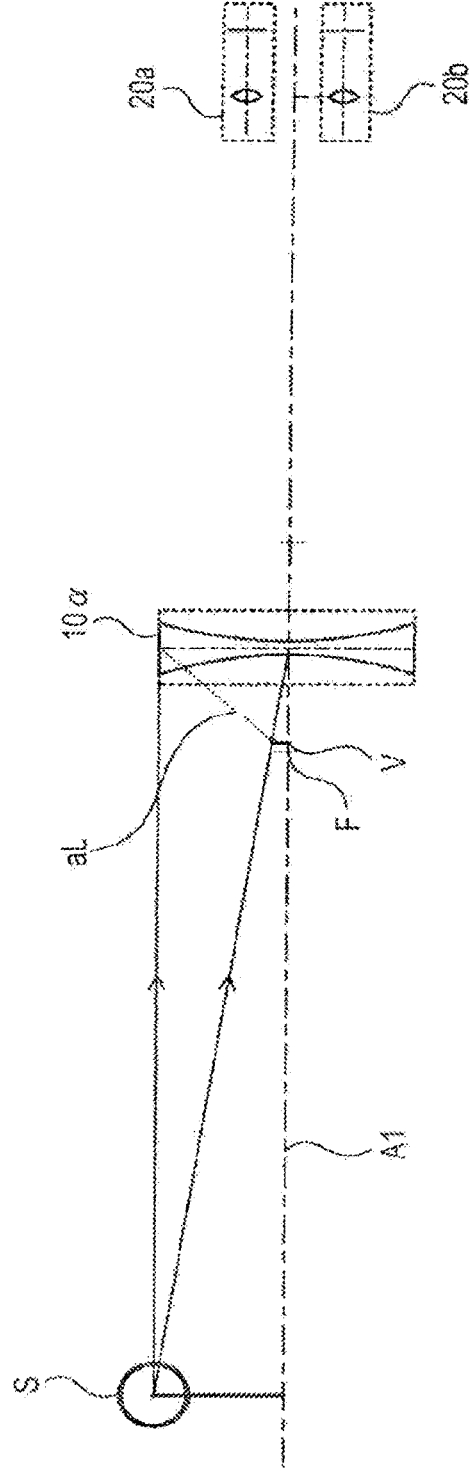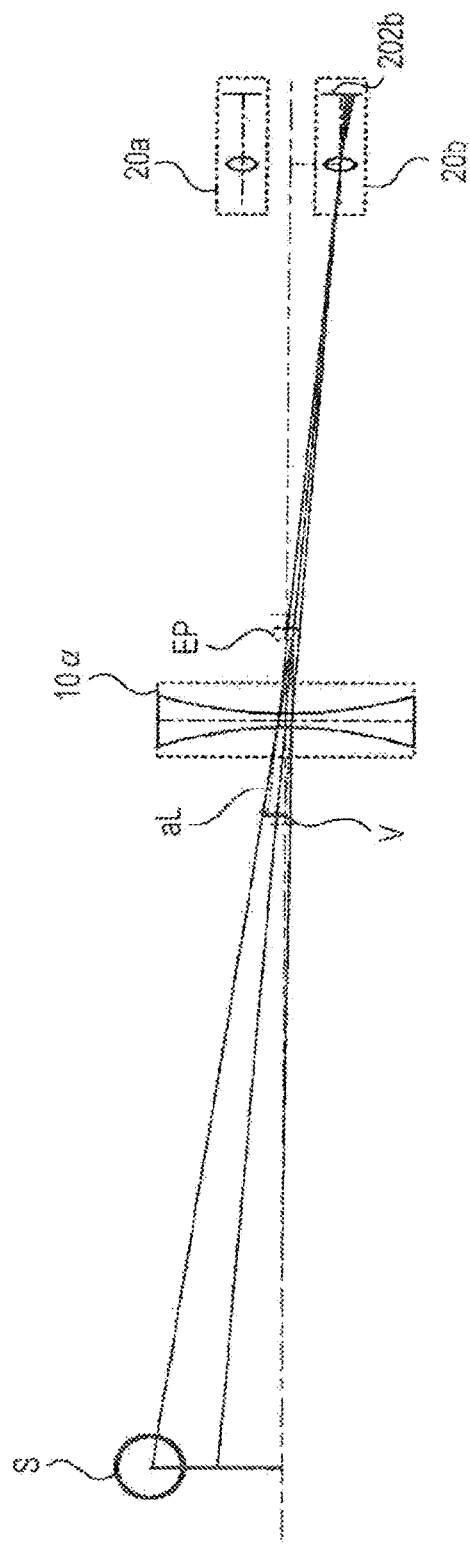

STEREOSCOPIC IMAGING APPARATUS

CROSS REFERENCE TO RELATED APPLICATIONS

This application is a continuation of U.S. application Ser. No. 13/287,712, filed Nov. 2, 2011, which is hereby incorporated by reference in its entirety. Foreign priority benefits are claimed under 35 U.S.C. 119(a)-(d) or 35 U.S. C. 365 (b) of Japanese Application No. 2010-251750, filed Nov. 10, 2010.

FIELD

The present disclosure relates to a stereoscopic imaging apparatus that shoots stereoscopic images, and specifically, to a technology of adjusting a base line length as a distance between lenses of plural lenses for imaging stereoscopic images.

BACKGROUND

Recently, demand for cameras (stereoscopic imaging apparatuses) that may shoot 3D (stereoscopic) images has been getting stronger. As an imaging method of stereoscopic images, a beam splitter method (half mirror method) of shooting using a half mirror, a side-by-side method (side-by-side twin-eye method) of shooting using two imaging apparatuses placed physically side by side, etc. are known. In these shooting methods, the imaging apparatuses are mounted on a pedestal called Rig for shooting, and the degree of freedom in mounting of the imaging apparatus is higher. For example, the distance between lenses of two lenses for shooting of stereoscopic images (base line length; hereinafter, referred to as IAD: InterAxial Distance), convergence, angle of view, etc. may be selected with the high degree of freedom.

However, while the degree of freedom is high, there is a problem that lots of efforts and time are necessary for setting and adjustment with respect to each shooting because the apparatuses are mounted on the rig. Further, there is a problem that the rig for the beam splitter method is significantly large-scaled and not suitable for use of shooting in the fields and interviews.

To solve the problems, two 2D video shooting cameras for shooting by the side-by-side method are incorporated in one housing to form an integrated two-eye 3D camera. The integrated two-eye 3D camera having the configuration does not need assembly or adjustment of alignment. Further, the camera is compact and easy to carry at shooting in the fields and interviews and has an advantage to promptly start shooting after setup in a short time.

However, the integrated two-eye 3D camera is basically according to the side-by-side method, and adjustment of IAD is limited. That is, the respective optical systems and imagers of the two eyes physically interfere with each other, and IAD is difficult to be made shorter than a certain distance determined depending on the placement positions of the optical systems and imagers. Accordingly, for example, in the case where shooting is performed very close to a subject, parallax when the subject is displayed on a 3D display several meters behind it exceeds the range of parallax when a human can comfortably view 3D images.

As the cases where the subject and the imaging apparatus is very close, for example, shooting of an interview of a person, shooting at the backyard in sports broadcasting, etc. are conceivable. In the cases, the distance between the subject and the imaging apparatus is about 1 to 2 m and the convergence point is set to the distance of 1 to 2 m. In the cases, the most useful IAD for bringing the parallax within the range in which a human can comfortably view 3D images is considered to be 10 mm to 40 mm. However, in the current two-eye 3D camera, it is difficult to realize the short IAD while keeping image quality and functions, i.e., without reducing the diameters of lenses or sizes of the imagers.

In the case where shooting is performed according to the above described beam splitter method, two imaging apparatuses do not physically interfere with each other and the IAD can be made very short. However, as described above, there is the problem that lots of efforts and time are necessary for setting and adjustment with respect to each shooting, and the problem that the method is not suitable for shooting of an interview of a person or shooting at the backyard in sports broadcasting still remains.

For example, in Patent Document 1 (JP-A-2003-5313) a stereoscopic image shooting apparatus in which the convergence point can be adjusted to an arbitrary position with the focus point of the camera coinciding with the convergence point of two eyes is described. Using the apparatus, shooting can be performed with the IAD equal to the pupil distance of a human and, in the case of close-in shooting, videos with natural stereoscopic effects may be shot.

SUMMARY

However, in the configurations described in Patent Document 1, specifically in FIGS. 3A and 3B and 5A, and 5B, for bringing the convergence point and the focus point to coincide with each other, it is considered to be necessary that the imaging optical system is focused on infinity. In this case, in normal shooting, i.e., shooting in the state of on-focus in which a moving subject is constantly focused on or the like, it is considered that the shot videos are very unnatural. For example, when the subject moves forward and backward, videos in which the subject itself does not move forward or backward, but the surrounding landscape moves forward and backward are shot. That is, in the stereoscopic image shooting apparatus described in Patent Document 1, there are problems that it is impossible to change the focus without changing the on-screen position or change the on-screen position without changing the focus.

Thus, it is desirable to perform shooting of stereoscopic images with a short base line length with image quality and functions maintained.

A stereoscopic imaging apparatus according to an embodiment of the present disclosure includes an objective optical system having a function of imaging a subject as a real image or a virtual image, and plural imaging optical systems that image plural subject luminous fluxes output from different paths of the objective optical system again as parallax images using plural independent optical systems. Further, in the case where a focal length value when the objective optical system images the subject as the real image is positive and the focal length value when the objective optical system images the subject as the virtual image is negative, a focal distance (f) of the objective optical system and a distance (L) from a rear principal point of the objective optical system to a front principal point of the imaging optical system is set to values that satisfy the following equation:

$$|f/(L-f)| \leq 1.$$

According to the configuration, substantial pupils (effective pupils) are formed between the subject and the objective optical system or between the objective optical system and the imaging optical systems, and images obtained through the effective pupils are imaged. Further, by setting the focal distance of the objective optical system and the distance (L) from the rear principal point of the objective optical system to the front principal point of the imaging optical system to the values that satisfy the above described equation, the distance between the effective pupils may be made shorter than an actual base line length determined depending on a distance between lenses of the plural imaging optical systems. Therefore, shooting of stereoscopic images may be performed with the shorter base line length while keeping image quality and functions without reducing the diameters of the lenses and the sizes of imagers of the imaging apparatus.

BRIEF DESCRIPTION OF THE DRAWINGS

FIGS. 3A and 3B are explanatory diagrams for explanation of a principle of formation of effective pupils according to one embodiment of the present disclosure, and FIG. 3A is an optical path diagram showing paths in which a beam in parallel to the optical axis of the beams radiated from a certain point of a subject and a beam passing through the lens center of an objective optical system travel and FIG. 3B is an optical path diagram showing paths in which beams radiated from the lens center of the imaging optical system travel.

FIGS. 5A and 5B are explanatory diagrams for explanation of a calculation method of an effective IAD according to one embodiment of the present disclosure, and FIG. 5A is an optical path diagram showing paths of beams in parallel to the optical axis of beams passing through the effective pupils and FIG. 5B extracts and shows only a part necessary for calculation of the effective IAD of the information shown in FIG. 5A.

FIG. 6A is an optical path diagram showing paths of beams in parallel to the optical axis of beams radiated from the lens centers of the imaging optical systems and FIG. 6B extracts and shows only a part necessary for calculation of the effective pupil positions of the information shown in FIG. 6A.

FIG. 7A shows an example when the imaging optical system IAD is taken narrower, FIG. 7B shows an example when the imaging optical system IAD is taken longer than that shown in FIG. 7A, and FIG. 7C shows an example when the imaging optical system IAD is taken longer than that shown in FIG. 7B.

FIG. 8A shows an example when the distance from the rear principal point of the objective optical system to the front principal point of the imaging optical system is taken wider, FIG. 8B shows an example when the distance from the rear principal point of the objective optical system to the front principal point of the imaging optical system is taken narrower than that shown in FIG. 8A, and FIG. 8C shows an example when the distance from the rear principal point of the objective optical system to the front principal point of the imaging optical system is taken narrower than that shown in FIG. 8B.

FIG. 9A shows an example when the focal length is taken narrower, FIG. 9B shows an example when the focal length is taken wider than that shown in FIG. 9A, and FIG. 9C shows an example when the focal length is taken wider than that shown in FIG. 9B.

FIGS. 13A and 13B are explanatory diagrams for explanation of a principle of formation of effective pupils according to the modified example of one embodiment of the present disclosure, and FIG. 13A is an optical path diagram showing paths in which a beam in parallel to the optical axis and a beam passing through the lens center of an objective optical system of the beams radiated from a certain point of the subject travel and FIG. 13B is an optical path diagram showing paths in which beams radiated from the lens center of the imaging optical system travel.

FIG. 15A is an optical path diagram showing paths of beams in parallel to the optical axis of beams passing through the effective pupils and FIG. 15B extracts and shows only a part necessary for calculation of the effective IAD of the information shown in FIG. 15A.

DETAILED DESCRIPTION

As below, embodiments for implementing the present disclosure will be explained. The explanation will be made in the following order.

1. Configuration Example of Stereoscopic Imaging apparatus

2. Various modified Examples

1. Configuration Example of Stereoscopic Imaging Apparatus

[Overall Configuration Example of Stereoscopic Imaging Apparatus]

Figure 1:
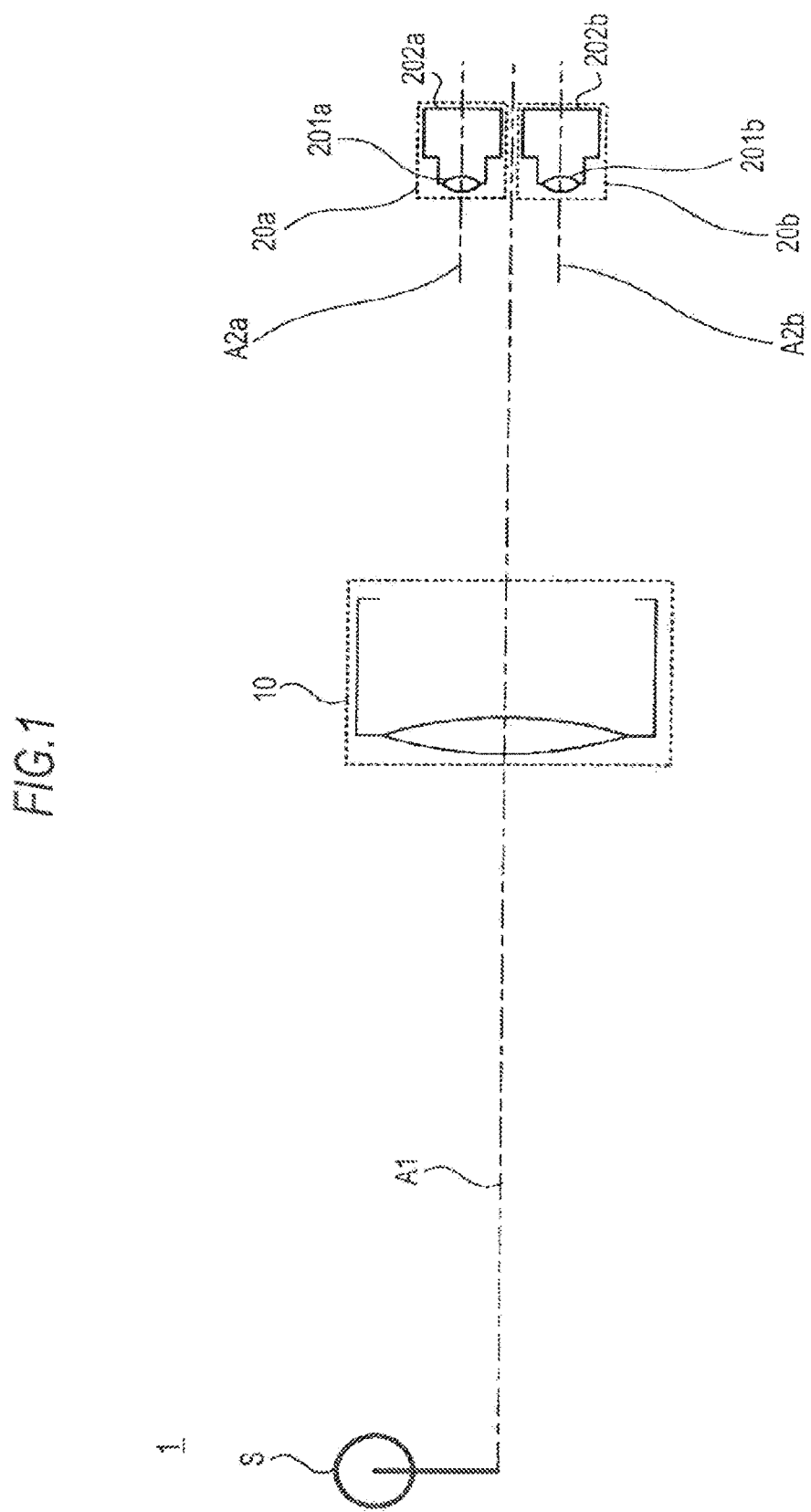
FIG. 1 is a block diagram showing a configuration example of a stereoscopic imaging apparatus according to one embodiment of the present disclosure.

FIG. 1 shows a configuration example of a stereoscopic imaging apparatus according to a first embodiment of the present disclosure. The stereoscopic imaging apparatus 1 includes an objective optical system 10 having a function of imaging a subject S as a real image and two imaging optical systems 20a, 20b that respectively image plural subject luminous fluxes output from different paths of the objective optical system 10 as parallax images again. In the embodiment, a convex lens is used for the objective optical system 10. Note that, in the example shown in FIG. 1, for the explanation to be easily understood, the objective optical system 10 is a thin lens having a focal length f, the imaging optical systems 20a, 20b include thin lenses 201a, 201b and imagers 202a, 202b, respectively. The actual objective optical system 10 includes multiple or multiple groups of lenses, filters, diaphragms, lens drive mechanisms, etc. Further, in addition to the mechanisms, a zoom function, a focusing function, and other functions may be provided. The imaging optical systems 20a, 20b also actually include multiple or multiple groups of lenses, filters, diaphragms, lens drive mechanisms, etc., and may have a zoom function, a focusing function, and other functions. In the configuration shown in FIG. 1, the objective optical system 10 and the imaging optical systems 20a, 20b are placed so that an optical axis A1 of the objective optical system 10 and optical axes A2a, A2b of the respective imaging optical system 20a, 20b may exist on the same plane.

[Formation Example of Effective IAD in Stereoscopic Imaging Apparatus]

Figure 2:
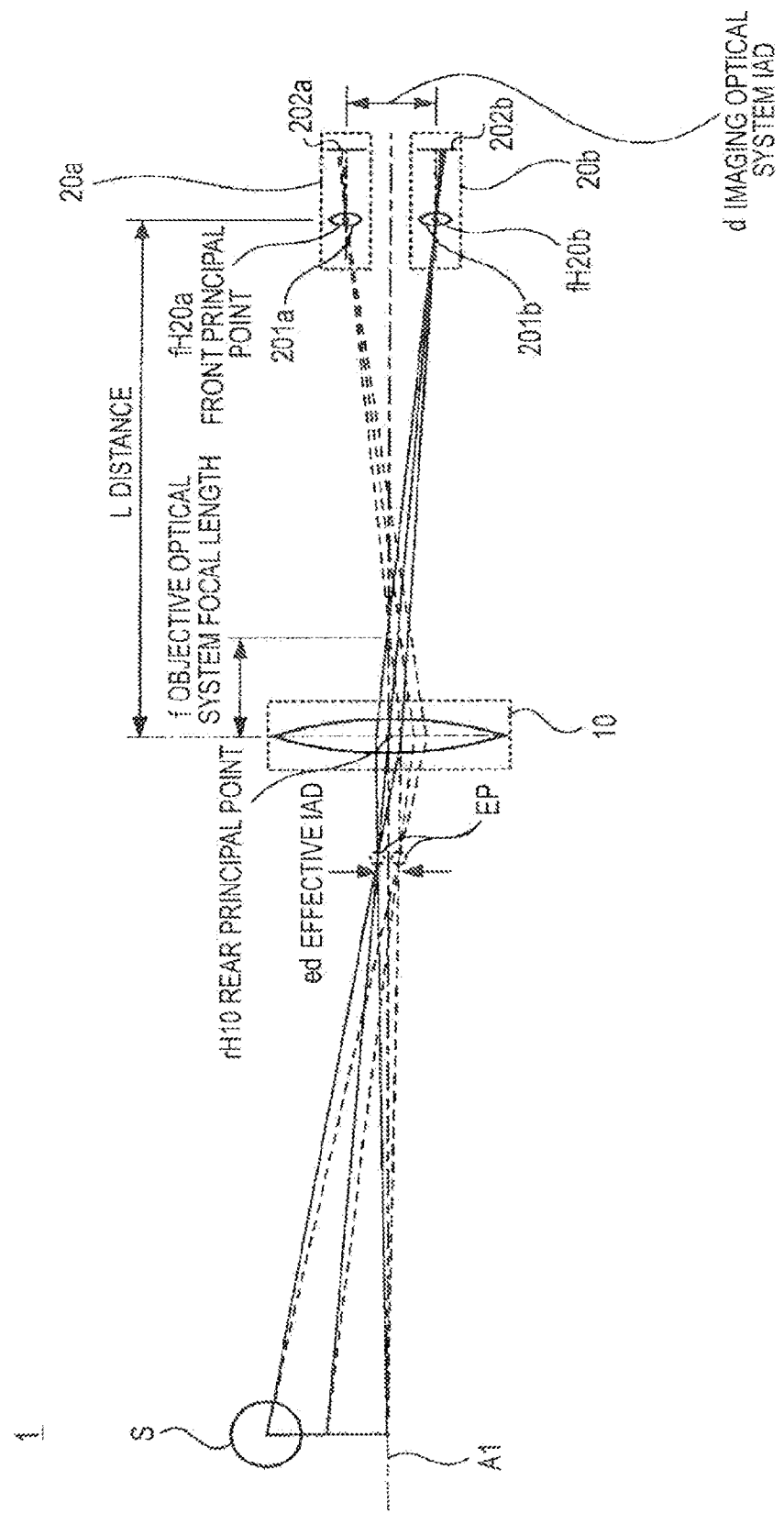
FIG. 2 is an optical path diagram showing paths in which beams passing through principal points of lenses of imaging optical systems of beams radiated from a subject travel according to one embodiment of the present disclosure.

Next, a substantial IAD (hereinafter, referred to as "effective IAD") formed in the stereoscopic imaging apparatus 1 will be explained with reference to FIG. 2. FIG. 2 is an optical path diagram showing paths in which beams passing through principal points of lenses of the imaging optical systems 20a, 20b of beams radiated from a subject S travel. The luminous fluxes radiated from the subject S are allowed to enter the objective optical system 10, then, guided by the two imaging optical systems 20a, 20b and imaged on the imagers 202a and 202b, and respectively form parallax images. In this regard, the beams passing through a front principal point fH20a of the lens of the imaging optical system 20a and the beams passing through a front principal point fH20b of the lens of the imaging optical system 20b are considered. For example, the group of beams passing through the principal point fH20a of the imaging optical system 20a are upper beams shown by broken lines and the beams passing through the principal point fH20b of the imaging optical system 20b are lower beams shown by solid lines. Further, the beams shown by the broken lines and the beams shown by the solid lines respectively pass through two effective pupils (hereinafter, referred to as effective pupils EP) virtually existing between the subject S and the objective optical system 10. Then, the subject S seen from the positions of the effective pupils EP is imaged on the imager 202a of the imaging optical system 20a and the imager 202b of the imaging optical system 20b. That is, the distance between these two effective pupils EP (hereinafter, referred to as "effective IADed") is the substantial IAD in the stereoscopic imaging apparatus 1. The principle of formation of the effective pupils EP between the subject S and the objective optical system 10 will be described later with reference to FIGS. 3A, 3B, and 4.

The effective IADed is expressed by the following equation 1.

$$ed = f/(L-f) \times d \quad \text{(Eq. 1)}$$

In the equation 1, "f" is a focal length of the objective optical system 10, "L" is a distance from a rear principal point rH10 of the objective optical system 10 to the front principal point fH20a of the imaging optical system 20a and the front principal point fH20b of the imaging optical system 20b. Note that, when the optical system is idealized as the thin lens as shown in FIG. 2, there is no distinction made between the front principal point and the rear principal point, and the front principal point and the rear principal point coincide with the principal point. Further, "d" is an IAD determined depending on the placement positions of the imaging optical system 20a and the imaging optical system 20b, and generally, refers to the distance between front principal points of the imaging optical systems, i.e., the distance between the front principal points fH20a and fH20b of the imaging optical system 20a and the imaging optical system 20b.

For example, the focal length f of the objective optical system 10 is 70 mm and the distance L is 370 mm. Further, the imaging optical system 20a and the imaging optical system 20b are separately placed at a distance d=60 mm with the optical axis A1 of the objective optical system 10 as an axis of symmetry (imaging optical system IADd=60 mm). In this case, the effective IADed is calculated to be 14 mm by the above equation 1. This means that, compared to the imaging optical system IADd (60 mm) obtained depending on the placement positions of the imaging optical systems 20a and 20b, the substantial IAD (effective IADed) may be made shorter to f/(L−f) times (14 mm).

Therefore, by setting the focal length f and the distance L of the objective optical system 10 to values that satisfy the following equation 2, the effective IADed may be made shorter than the imaging optical system IADd obtained depending on the placement positions of the imaging optical systems 20a and 20b. Note that the following equation is on the assumption that a convex lens is used as the lens of the objective optical system 10 and its focal length f is positive (f>0).

$$f/(L-f) \le 1 \quad \text{(Eq. 2)}$$

[Principle of Formation of Effective Pupils in Stereoscopic Imaging Apparatus]

Figure 4:
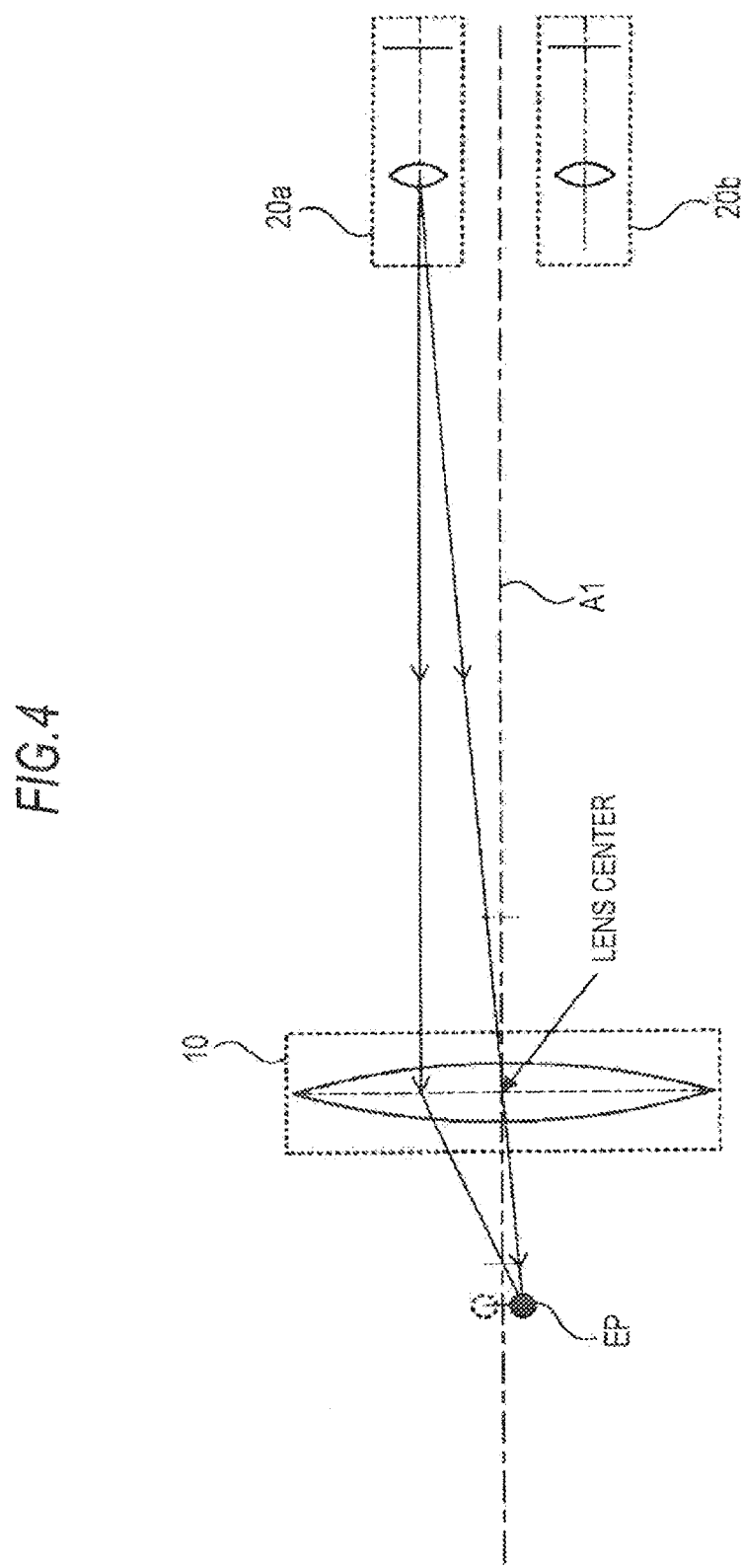
FIG. 4 is an optical path diagram showing paths in which a beam in parallel to the optical axis and a beam passing through the lens center of the objective optical system of beams radiated from the lens center of the imaging optical system travel according to one embodiment of the present disclosure.

Next, in the stereoscopic imaging apparatus 1, the principle of virtual formation of effective pupils between the subject S and the objective optical system 10 will be explained with reference to FIGS. 3A, 3B, and 4. First, a spatial image S' formed by the objective optical system 10 will be explained with reference to FIG. 3A, and then, beam paths from the subject S to the imager 202a (202b) will be explained with reference to FIG. 3B. Then, a mechanism of formation of the effective pupils will be explained with reference to FIG. 4.

(1) Regarding Spatial Image

As shown in FIG. 3A, the luminous fluxes radiated from the subject S pass through the objective optical system 10 and is imaged again, and thereby, the spatial image S' is formed between the objective optical system 10 and the imaging optical systems 20a, 20b. The spatial image S' is seen as if there was an object in its position, and may be seen from the view points of the lenses of the imaging optical systems 20a, 20b. The principle of formation of the spatial image S' is easily understood by considering two beams of a beam in parallel to the optical axis A1 of the beams radiated from a certain point of the subject S and a beam passing through the center of the lens of the objective optical system 10. The beam in parallel to the optical axis A1 of the beams output from a certain point of the subject S becomes a beam passing through the focal point F of the objective optical system 10 after passing through the lens because of the property of the lens of the objective optical system 10. On the other hand, the beam passing through the center of the lens of the objective optical system 10 travels in a straight line without change because of the property of the lens. Then, these two beams intersect at another point again.

The intersection point is a point in the spatial image S' corresponding to the subject S that has radiated the beams.

(2) Beam Paths from Subject to Imager of Imaging Optical System

As shown in FIG. 3B, if beams are radiated from the centers of the lenses of the imaging optical systems 20a, 20b, the beams radiated from the subject S travel in the same paths as those of those beams. Accordingly, the paths are easily understood by consideration from the centers of the lenses of the imaging optical systems 20a, 20b. In the example shown in FIG. 3B, the path in which the beam radiated from the center of the lens of the imaging optical system 20a travels will be explained as an example. The beam radiated from the center of the lens of the imaging optical system 20a passes through a certain point of the spatial image S', then, reaches the lens of the objective optical system 10, and travels toward a certain point of the subject S corresponding to "certain point of spatial image S'". The beam from the center of the lens of the imaging optical system 20a to the imager 202a may be obtained by extending the beam passing through the lens center of the imaging optical system 20a to the position of the imager 202a without change.

(3) Regarding Effective Pupils

Subsequently, the principle of formation of the effective pupils EP will be explained with reference to FIG. 3B. The creation of the beam path from the subject S to the imager 202a of the imaging optical system 20a as described above is performed with respect to the beams passing through other points of the spatial image S'. Then, it is known that the beams radiated from the lens center of the imaging optical system 20a intersect at a certain point again after passing through the objective optical system 10. This point is the effective pupil EP. The effective pupil EP is a point that all beams to pass through the lens center of the imaging optical system 20a pass. Accordingly, the picture imaged on the imaging surface of the imager 202a of the imaging optical system 20a is a picture equal to an image shot using the effective pupil EP as a pupil. That is, by imaging the subject S using the stereoscopic imaging apparatus 1 according to the embodiment, the same picture as the picture shot by a camera placed in the position of the effective pupil EP can be acquired.

The position where the effective pupil EP is formed may be obtained also by considering the beam in parallel to the optical axis A1 of the beams radiated from the lens center of the imaging optical system 20a and the beam passing through the lens center of the objective optical system 10. As described above, if beams are radiated from the center of the lens of the imaging optical system 20a, the beams radiated from the subject S travel in the same paths as the paths in which those beams travel. This means that, if a light emitting point is placed at the lens center of the imaging optical system 20a, all of the beams radiated from the point pass through the effective pupil EP. That is, the effective pupil EP is "shadow of lens" or "spatial image" of the imaging optical system 20a. Therefore, as shown in FIG. 4, it is known that the effective pupil EP is formed at the point at which the beam in parallel to the optical axis A1 of the beams radiated from the lens center of the imaging optical system 20a and the beam passing through the lens center of the objective optical system 10 intersect again.

[Calculation Method of Effective IAD]

As described above, the effective pupil EP is the point at which all beams from the subject S toward the lens center of the imaging optical system 20a (20b) pass. These beams include beams in parallel to the optical axis A1. To obtain the effective IADed, consideration of the beams in parallel to the optical axis A1 is easily understood. In FIG. 5A, the paths of the beams in parallel to the optical axis A1 of the beams passing through the effective pupils EP are shown by broken lines. The beams in parallel to the optical axis A1 passing through the effective pupils EP pass through the lens of the objective optical system 10, and then, travel toward the focal point F of the lens of the objective optical system 10 because of the property of the lens. The beams that have passed through the focal point F travel toward the centers of the respective lenses of the imaging optical systems 20a, 20b according to the definition of the effective pupils EP.

FIG. 5B extracts only a characteristic part necessary for obtainment of the effective IADed of the information shown in FIG. 5A. In the drawing, two triangles having similarity shapes to each other are shown. One is a shaded larger triangle having a bottom side of the imaging optical system IADd as the distance between the respective lenses of the imaging optical systems 20a, 20b and a height of (distance L—objective optical system focal length f). The other one is a hatched smaller triangle having a bottom side of the effective IADed as the distance between the two effective pupils EP and a height of the focal length f of the objective optical system 10. These two triangles have similarity shapes to each other, and they are expressed by the following equations because of their property.

Effective IADed: Imaging optical system
IADd=Objective optical system focal length $f$:
Distance $L$–Objective optical system focal length $f$ Therefore, $ed \times (L-f) = f \times d$, and $$ed = f/(L-f) \times d \qquad \text{Eq. (1)}$$

is calculated.

Figure 6A:
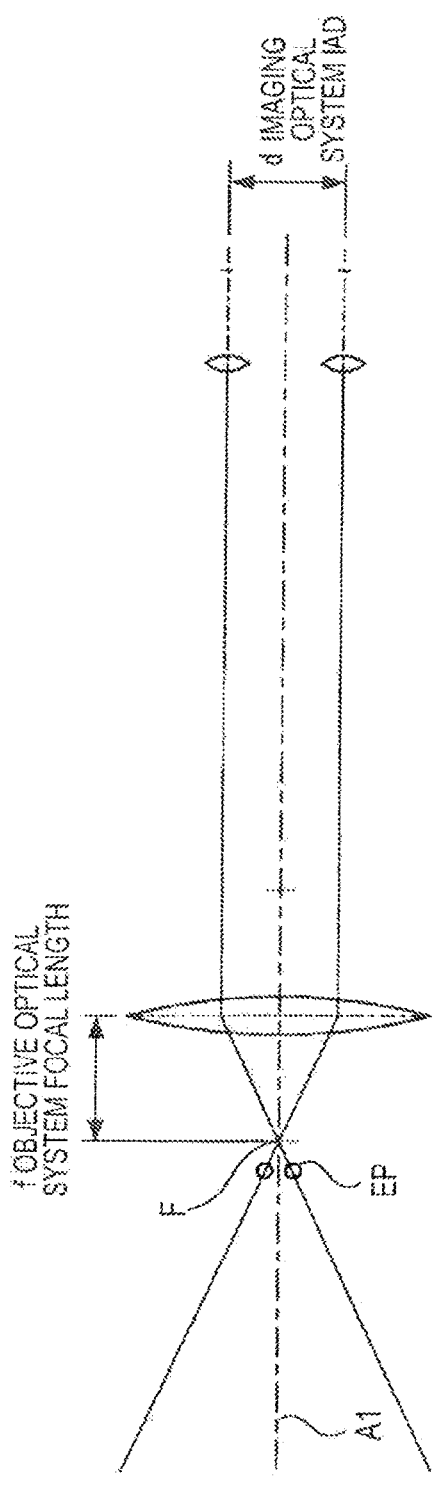
FIGS. 6A and 6B are explanatory diagrams for explanation of a calculation method of effective pupil positions according to one embodiment of the present disclosure.

The position of the effective pupil EP in the optical axis direction may be calculated using the focal length f of the lens of the objective optical system 10, the imaging optical system IADd, and the effective IADed. FIG. 6A shows paths of beams in parallel to the optical axis A of beams radiated from the respective lens centers of the imaging optical systems 20a, 20b. The beam radiated from the center of the lens of the imaging optical system 20a and the beam radiated from the center of the lens of the imaging optical system 20b reach the lens of the objective optical system 10 and pass through the lens, and becomes beams passing through the focal point F of the objective optical system 10. Then, after passing through the focal point F, the beams respectively pass through the two effective pupils EP and travel toward the subject S (not shown).

Figure 6B:
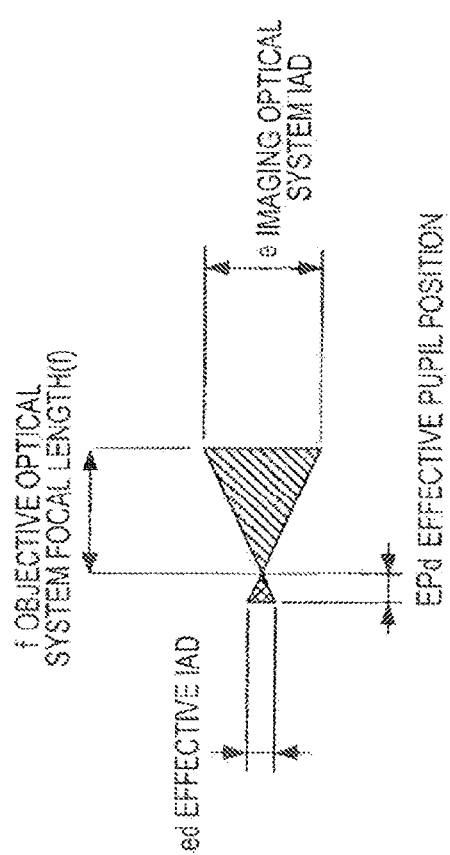

FIG. 6B extracts only a characteristic part necessary for obtainment of the positions of the effective pupils in the optical axis direction of the information shown in FIG. 6A. In the drawing, two triangles having similarity shapes to each other are shown. One is a shaded larger triangle having a bottom side of the imaging optical system IADd and a height of the effective pupil objective optical system focal length f. The other one is a hatched smaller triangle having a bottom side of the effective IADed and a height of the distance from the focal point F to the effective pupil EP (hereinafter, referred to as "effective pupil position EPd"). These two triangles have similarity shapes to each other, and they are expressed by the following equations because of their property.

Effective IADed: Imaging optical system
IADd=Effective pupil position EPd: Objective optical system focal length $f$ Therefore, $$ed \times f = d \times EPd, \text{ and}$$

$$EPd = (ed \times f)/d \quad \text{Eq. (3)}$$

is calculated.

Next, formation examples of the effective IADed according to the stereoscopic imaging apparatus 1 of the embodiment will be explained with reference to FIGS. 7A to 9C. The effective IADed may be calculated using the above described equation 1. That is, by changing the objective optical system focal length f, the distance L, and the imaging optical system IADd, the effective IADed may be changed. That is, by changing these parameters, the effective IADed having an arbitrary length may be realized.

Figure 7A:
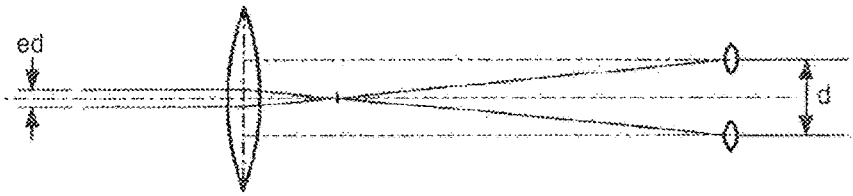
FIGS. 7A to 7C are explanatory diagrams showing changes of the effective IAD when the width of an imaging optical system IAD is changed according to one embodiment of the present disclosure.
Figure 7B:
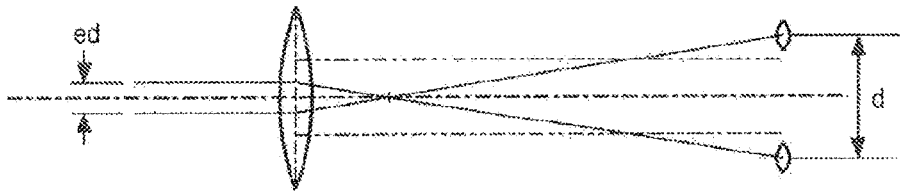
Figure 7C:
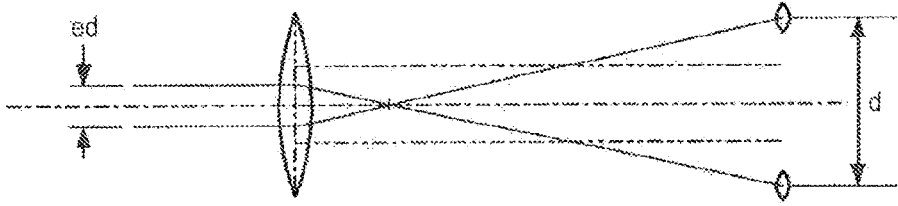

FIGS. 7A to 7C show examples when the width (length) of the effective IADed is changed by changing the imaging optical system IADd (the distance between the respective lenses of the imaging optical systems 20a, 20b). The same signs are assigned to the parts corresponding to those in FIG. 2, and their detailed explanation will be omitted. FIG. 7A shows an example when the imaging optical system IADd is set narrower (to the width shown in FIGS. 1 to 6B) and FIG. 7B shows an example when the imaging optical system IADd is made wider than that shown in FIG. 7A. FIG. 7C shows an example when the imaging optical system IADd is made wider than that shown in FIG. 7B. As shown in FIGS. 7A to 7C, it is known that the wider the imaging optical system IADd, the wider the effective IADed.

Figure 8A:
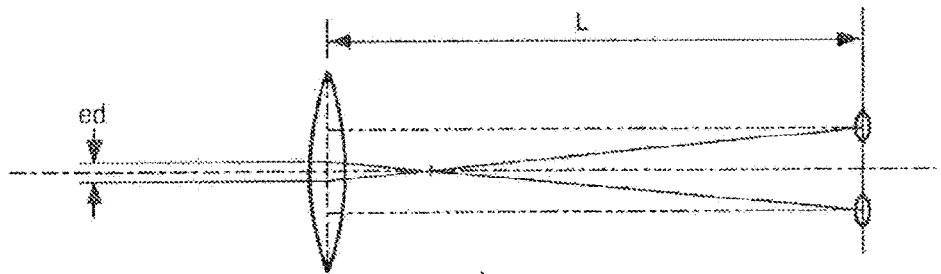
FIGS. 8A to 8C are explanatory diagrams showing changes of the effective IAD when the distance from the rear principal point of the objective optical system to the front principal point of the imaging optical system.
Figure 8B:
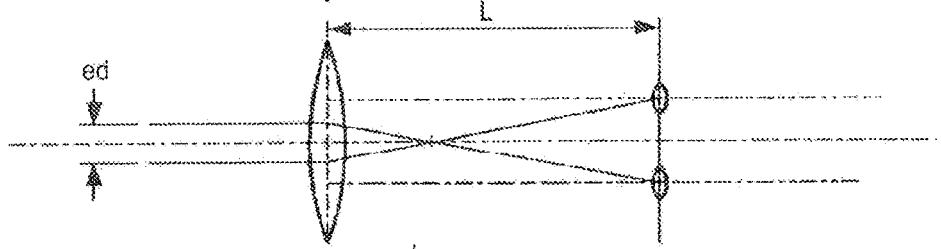
Figure 8C:
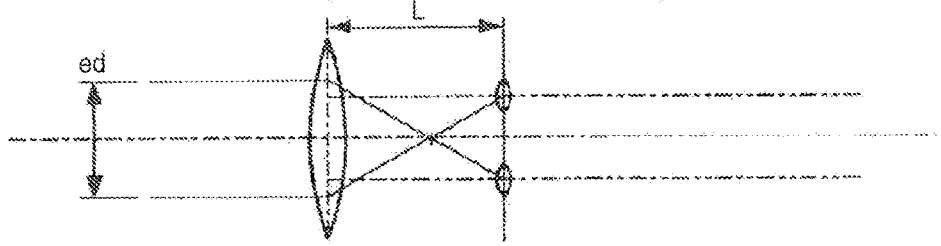

FIGS. 8A to 8C show examples when the width of the effective IADed is changed by changing the distance L (the distance from the rear principal point rH10 of the objective optical system 10 to the front principal point fH20a (fH20b) of the imaging optical system 20a (20b)). The same signs are assigned to the parts corresponding to those in FIG. 2, and their detailed explanation will be omitted. FIG. 8A shows an example when the distance L is taken wider and FIG. 8B shows an example when the distance L is made shorter than that shown in FIG. 8A. Further, FIG. 8C shows an example when the distance L is made shorter than that shown in FIG. 8B. As shown in FIGS. 8A to 8C, it is known that the shorter the distance L, the wider the effective IADed.

Note that, as shown in FIG. 8C, by setting the distance L (and the focal length·f) to satisfy f/(L−f)>1, the effective IADed can be made wider than the imaging optical system IADd. For example, the focal length f of the objective optical system 10 is 70 mm, the distance L is 105 mm, and the Imaging optical system IADd is 60 mm. In the case of the configuration, the imaging optical system IADd is calculated to be 120 mm by the above described equation 1. That is, compared to the imaging optical system IADd (60 mm) obtained depending on the placement positions of the imaging optical systems 20a and 20b, the effective IADed may be made longer to f/(L−f) times.

Figure 9A:
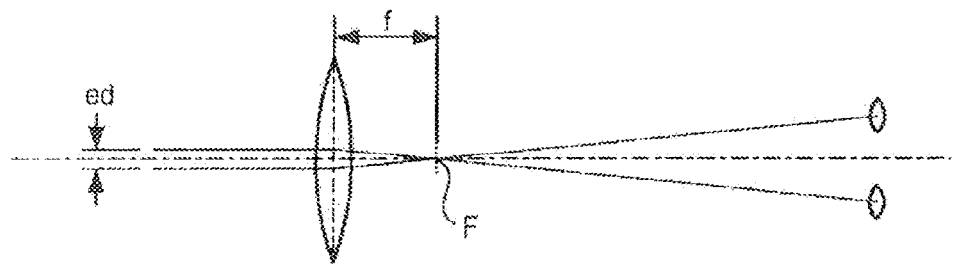
FIGS. 9A to 9C are explanatory diagrams showing changes of the effective IAD when the focal length of the objective optical system is changed according to one embodiment of the present disclosure.
Figure 9B:
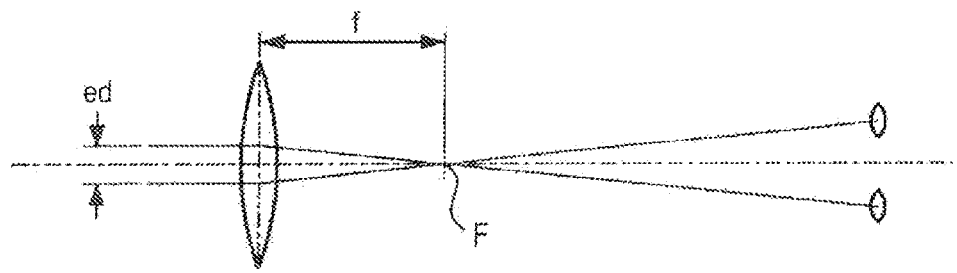
Figure 9C:
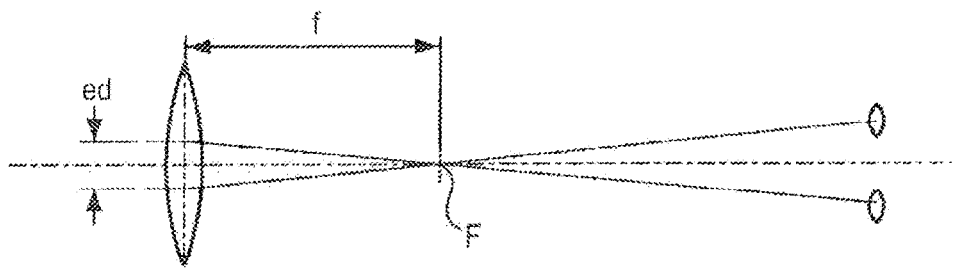

FIGS. 9A to 9C show examples when the effective IADed is changed by changing the focal length f of the objective optical system 10. The focal length f may be changed by using lenses with different focal lengths f and using zoom lenses. In FIGS. 9A to 9C, the same signs are assigned to the parts corresponding to those in FIG. 2, and their detailed explanation will be omitted. FIG. 9A shows an example when the focal length f is made narrower, and FIG. 9B shows an example when the focal length f is made longer than that shown in FIG. 9A. Further, FIG. 9C shows an example when the focal length f is made longer than that shown in FIG. 9B. As shown in FIGS. 9A to 9C, it is known that the longer the focal length f of the lens of the objective optical system 10, the wider the effective IADed.

As described above, according to the stereoscopic imaging apparatus 1 of the embodiment, by selecting the focal length f of the objective optical system 10, the parameter (distance L) related to the positions of the imaging optical systems 20a, 20b, and the imaging optical system IADd, the substantial IAD of the stereoscopic imaging apparatus 1 may be selected. Therefore, the degree of freedom of design of the stereoscopic imaging apparatus 1 may be improved.

Further, by setting the focal length f of the lens of the objective optical system 10 and the distance L to values that satisfy the equation 2, the substantial IAD (effective IADed) may be made shorter than the actual IAD (imaging optical system IADd) determined depending on the placement positions of the imaging optical systems 20a and 20b. Therefore, the range of parallax within one screen may be limited within a fixed range. Thereby, contents that impose large burdens on viewers such as contents having large amounts of pop out and depths from the screen and contents with parallax that largely changes at times when the scene changes are not shot. Thus, discomfort of eye strain and typical fatigue that viewers viewing the contents feel may be reduced. Furthermore, the important IAD from 10 mm to 40 mm most frequently used when near distance shooting is performed may be easily realized.

In addition, the effective IADed of the stereoscopic imaging apparatus 1 may be made shorter without bringing the placement positions of the imaging optical systems 20a and 20b closer, and thus, it is not necessary to reduce the sizes of the imagers or attach lenses having smaller diameters. That is, the effective IADed of the stereoscopic imaging apparatus 1 may be made shorter without deterioration of the performance of the camera main body such as resolution and sensitivity. Therefore, even in the stereoscopic imaging apparatuses of the side-by-side method and the integrated method that are difficult to reduce the distance between lenses, shooting with the shorter IAD may be easily performed.

Further, by setting the focal length f of the lens of the objective optical system 10 and the distance L to satisfy f/(L−f)>1, the effective IADed can be made wider than the imaging optical system IADd. According to the configuration, even in an apparatus that may only have a physically narrow IAD such as an endoscope, for example, videos with more stereoscopic effects may be shot.

Figure 10:
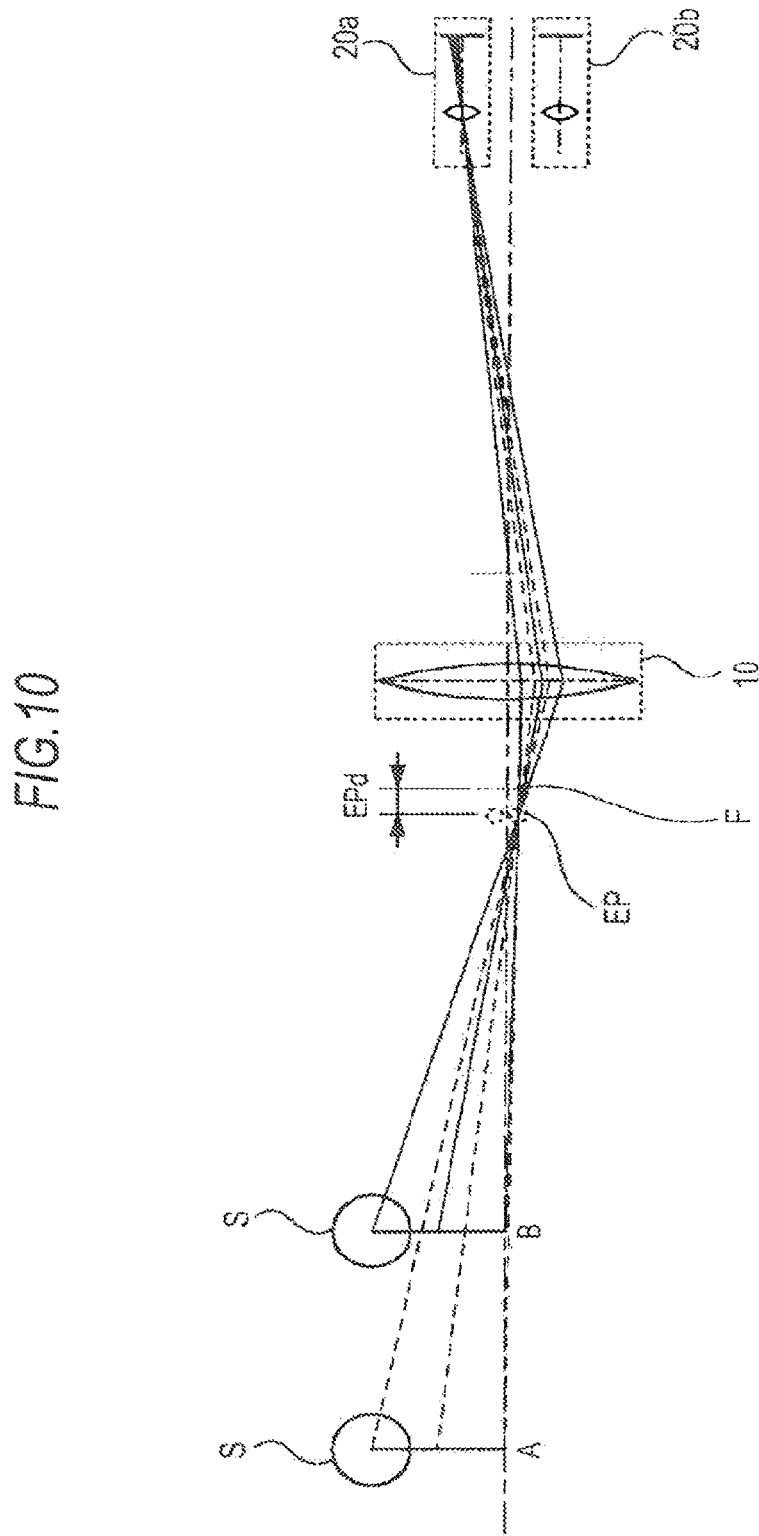
FIG. 10 is an optical path diagram showing paths in which beams radiated from the subject and passing through the lens center of the imaging optical system pass when the subject moves in the optical axis direction according to one embodiment of the present disclosure.

Furthermore, the effective pupil EP formed in the stereoscopic imaging apparatus 1 are the points at which all beams from the subject S toward the lens centers of the imaging optical systems 20a, 20b pass. Accordingly, for example, even when the subject S moves from position A to position B as shown in FIG. 10, all of the beams radiated from the position of the subject S in the position B and passing through lens centers of the imaging optical systems 20a, 20b pass through the effective pupils EP. Thereby, even when the subject S is movable, the same moving images as those when the camera is placed in the effective pupil position EPd may be shot. Therefore, functions of moving focus (focus position) of the imaging optical systems 20a, 20b to a desired position within a finite distance and control it can be additionally provided. Accordingly, for example, the focal lengths of the two imaging optical systems 20a, 20b may be controlled in a ganged manner and shooting may be performed constantly in focus on the moving subject S. By performing the shooting, normal and natural videos in which the subject S on the display screen moves forward and backward to the movement of the subject S may be shot.

In addition, according to the stereoscopic imaging apparatus 1 of the embodiment, unlike the technology shown as Patent Document 1, it is not necessary to constantly bring the convergence point and the focus to coincide with each other. Therefore, the convergence point may be adjusted by the imaging optical system 20a (20b) or the objective optical system 10, the focus may be adjusted by the imaging optical system 20a (20b) or the objective optical system 10, and the angle of view may be adjusted by the imaging optical system 20a (20b) or the objective optical system 10. That is, the parameters for shooting may be set by individually adjusting the objective optical system 10 and the imaging optical system 20a (20b).

2. Various Modified Examples

Figure 11:
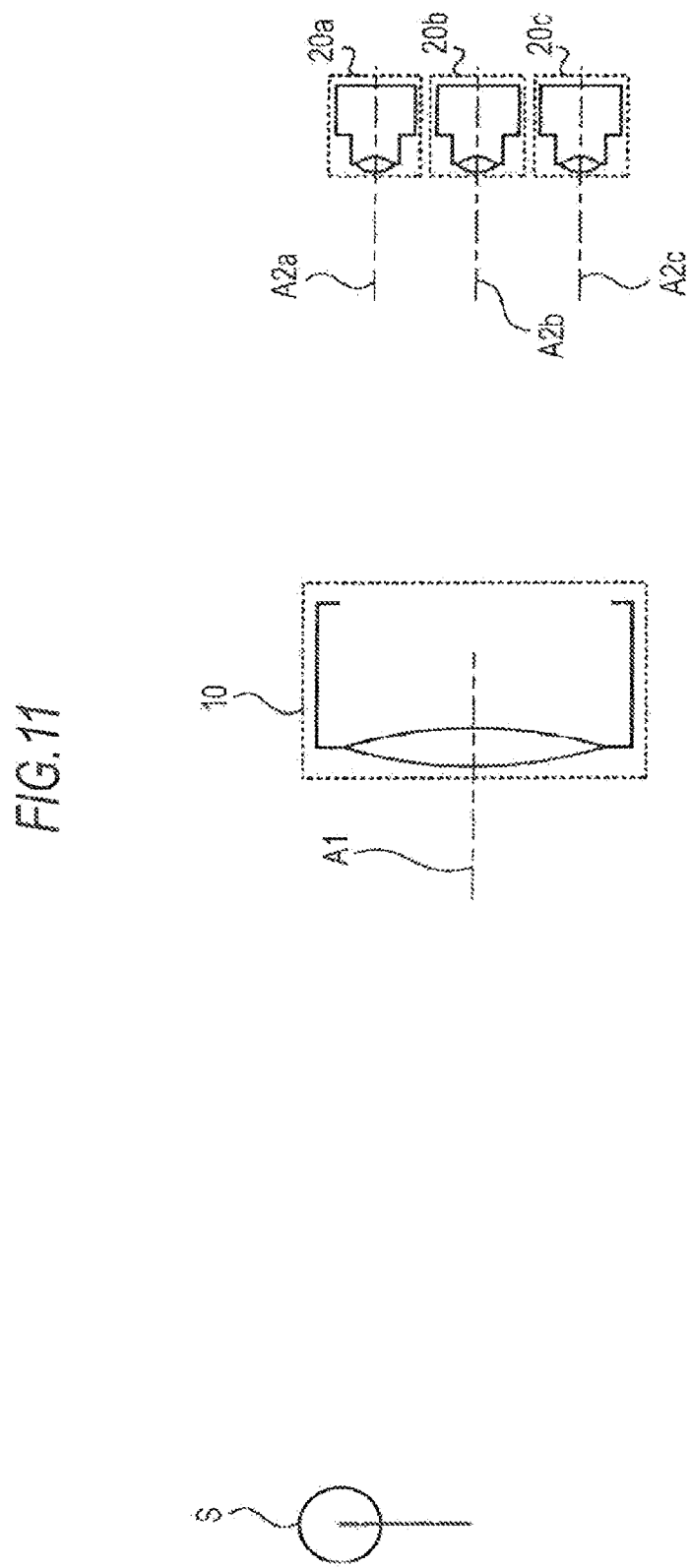
FIG. 11 is a block diagram showing a configuration example of a stereoscopic imaging apparatus according to a modified example of one embodiment of the present disclosure.
Figure 16:
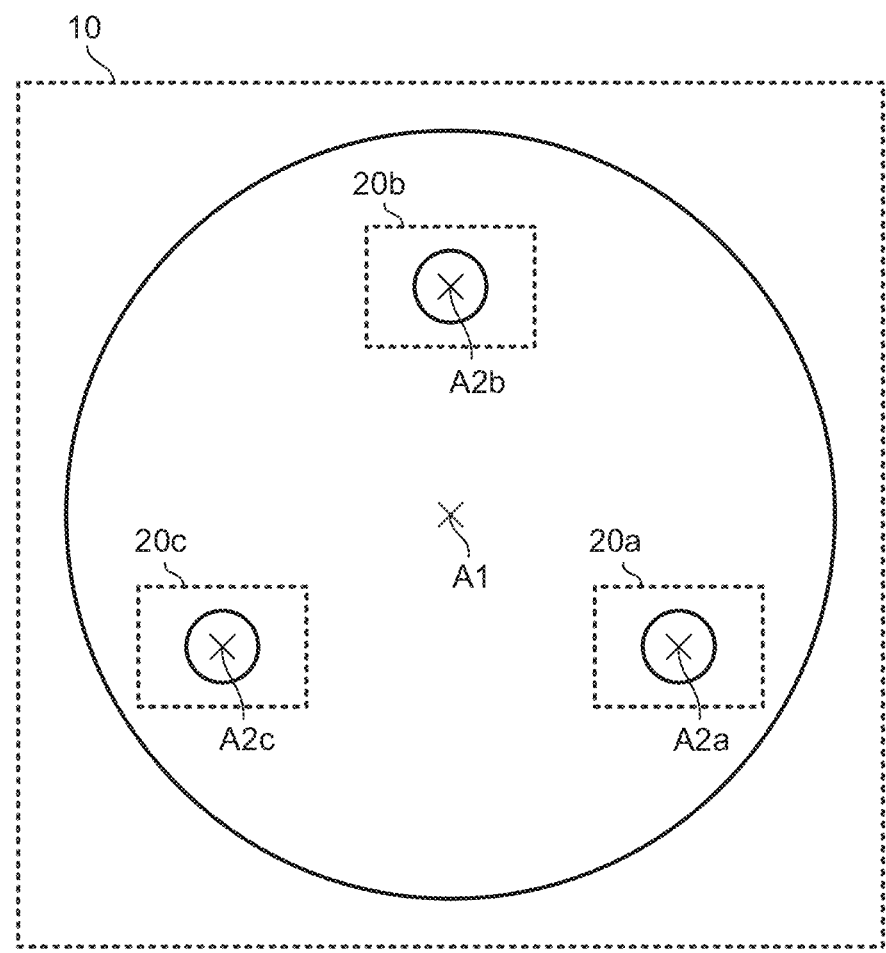
FIG. 16 depicts an end-on view arrangement of imaging optical systems and an objective optical system.

In the above described embodiment, the example in which the two imaging optical systems are provided has been cited, however, more of them may be provided. For example, as shown in FIG. 11, three of them may be provided such as imaging optical systems 20a, 20b, 20c. Further, the objective optical system 10 and the imaging optical systems 20a, 20b, 20c may be placed so that the optical axis A1 of the objective optical system 10 and the respective optical axes A2a, A2b, A2c of the imaging optical systems 20a, 20b, 20c may exist on different planes, as depicted in FIG. 16. According to the configuration, parallax information in the vertical direction may be obtained, and, for example, shooting when assuming that a viewer of stereoscopic images views the images in a posture of lying down or the like may be performed.

Figure 12:
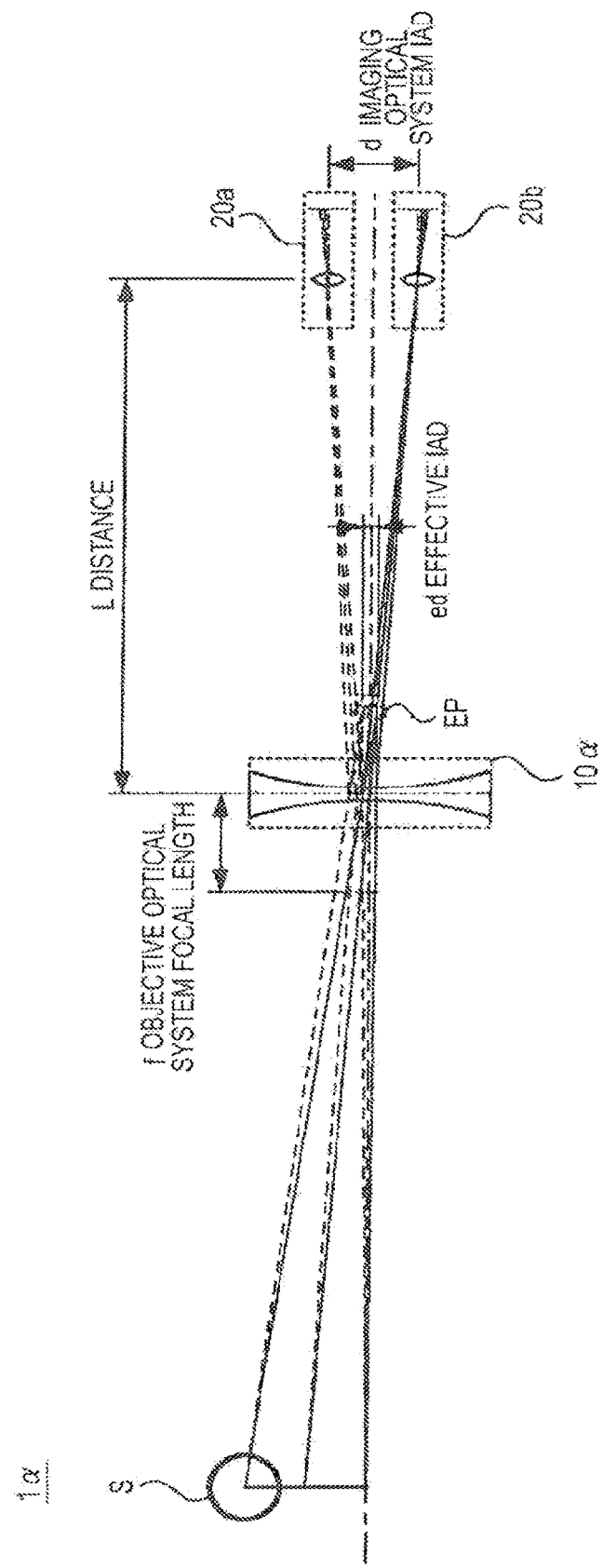
FIG. 12 is an optical path diagram showing paths in which beams passing through the principal points of lenses of imaging optical systems of beams radiated from a subject travel according to a modified example of one embodiment of the present disclosure.

Further, in the above described embodiment, the example in which the convex lens is used for the lens of the objective optical system 10 has been cited for explanation, however, a concave lens may be used. Configuration examples using a concave lens will be explained with reference to FIGS. 12 to 15B. FIG. 12 shows a configuration example of a stereoscopic imaging apparatus when a concave lens is used for an objective optical system. In FIG. 12, the same signs are assigned to parts corresponding to those in FIG. 2, and their detailed explanation will be omitted. In the example shown in FIG. 12, a concave lens is used as a lens of an objective optical system 10α, and the focal length f is formed nearer the subject side S. Accordingly, the effective pupils EP are formed between the objective optical system 10α and the imaging optical system 20a and the imaging optical system 20b.

FIGS. 13A and 13B are diagrams for explanation of a principle of formation of the effective pupils EP between the objective optical system 10α and the imaging optical systems 20a, 20b in an stereoscopic imaging apparatus 1α using the concave lens. In FIGS. 13A and 13B, the same signs are assigned to parts corresponding to those in FIGS. 3A and 3B, and their detailed explanation will be omitted. In the case where the concave lens is used for the objective optical system, a virtual image V is formed between the subject S and the objective optical system 10α. As is the case explained with reference to FIGS. 3A and 3B, the position in which the virtual image V is formed is easily understood by considering two beams of a beam in parallel to the optical axis A1 of the beams radiated from a certain point of the subject S and a beam passing through the center of the lens of the objective optical system 10α. As shown in FIG. 13A, the virtual image V is formed in a position in which an auxiliary line aL drawn from the point at which the beam in parallel to the optical axis A1 collides with the lens of the objective optical system 10α toward the focal point F of the objective optical system 10α and the beam passing through the center of the lens of the objective optical system 10α intersect.

FIG. 13B shows paths in which beams radiated from the center of the lens of the imaging optical system 20b travel. The actual beams radiated from the lens center of the imaging optical system 20b travel toward the subject S in the paths shown by solid lines. On the other hand, apparent beams when seen from the view point on the lens of the imaging optical system 20b pass through the objective optical system 10α, and then, travel toward the virtual image V in the path shown by auxiliary lines aL shown by broken lines. Further, the apparent beams certainly pass through the effective pupil EP in the position located in extension of the auxiliary line aL in an opposite direction to the objective optical system 10α. That is, the video formed on the imager 202b of the imaging optical system 20b is equal to a video shot using the effective pupil EP as a pupil.

Figure 14:
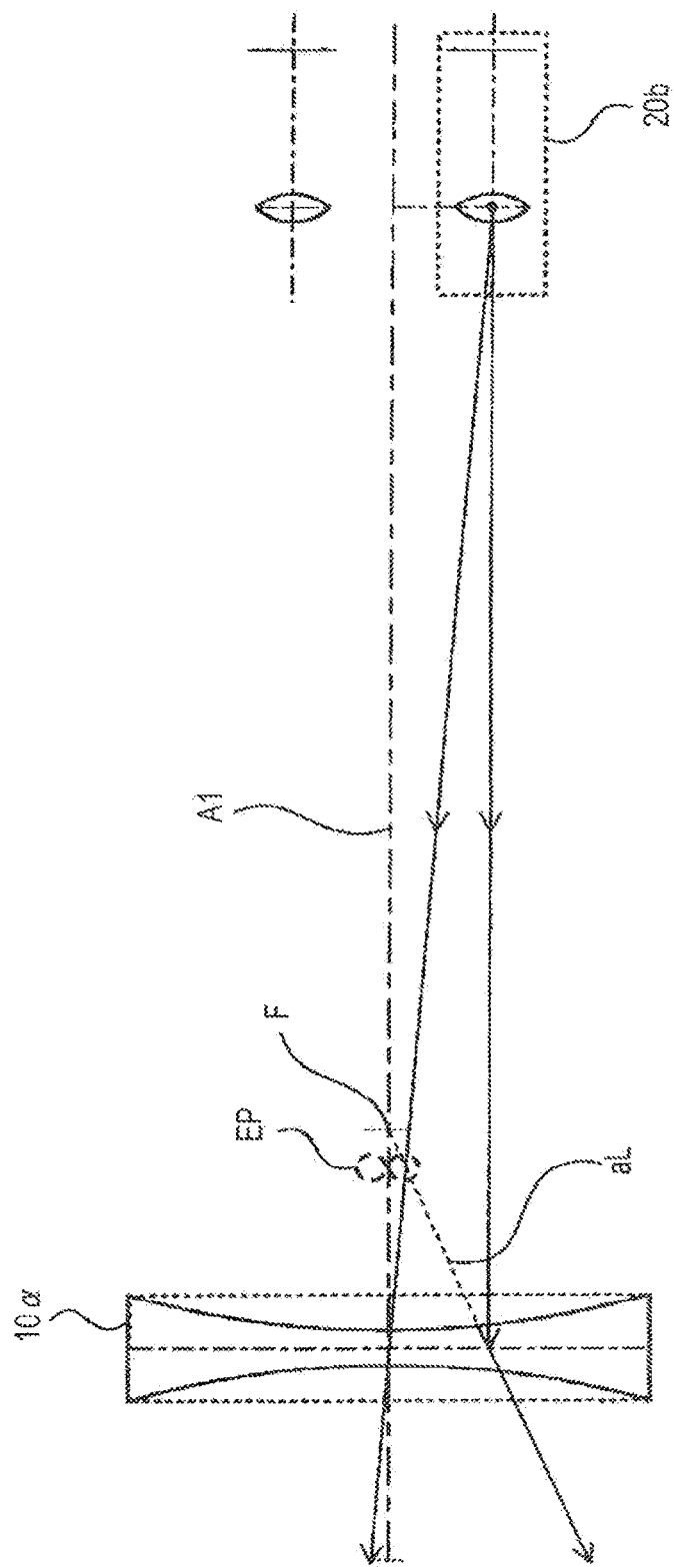
FIG. 14 is an optical path diagram showing paths in which a beam in parallel to the optical axis and a beam passing through the lens center of the objective optical system of beams radiated from the lens center of the imaging optical system travel according to the modified example of one embodiment of the present disclosure.

Furthermore, even in the case of using the concave lens, the positions in which the effective pupils EP are formed may be obtained by consideration of the beam in parallel to the optical axis A1 of the beams radiated from the lens center of the imaging optical system 20b and the beam passing through the lens center of the lens of the objective optical system 10α. FIG. 14 shows paths in which beams radiated from the center of the lens of the imaging optical system 20b travel. In FIG. 14, the same signs are assigned to the parts corresponding to those in FIG. 4, and their detailed explanation will be omitted. In FIG. 14, an auxiliary line aL between the focal point F of the objective optical system 10α and the point at which the beam in parallel to the optical axis A1 collides with the lens of the objective optical system 10α is shown by a broken line. Further, an effective pupil EP is formed in a position in which the beam radiated from the center of the lens of the imaging optical system 20b and shown by a solid line and the auxiliary line aL intersect. This means that, if a light emitting point is placed at the lens center of the imaging optical system 20b, all beams radiated from the point pass through the effective pupil EP. That is, the effective pupil EP is "shadow of lens" or "virtual image" of the imaging optical system 20b.

Figure 15A:
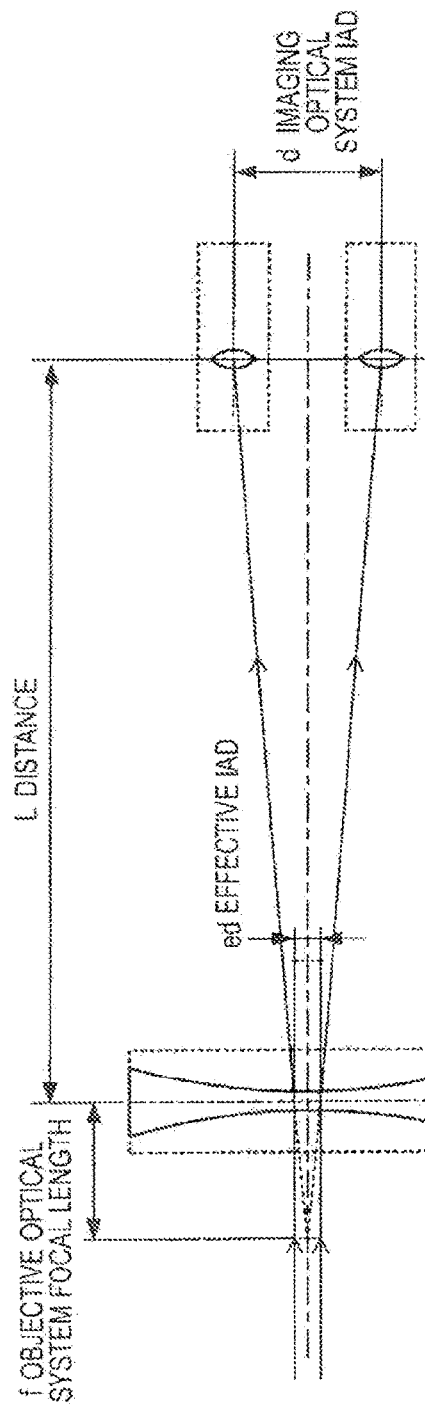
FIGS. 15A and 15B are explanatory diagrams for explanation of a calculation method of an effective IAD according to the modified example of one embodiment of the present disclosure.
Figure 15B:
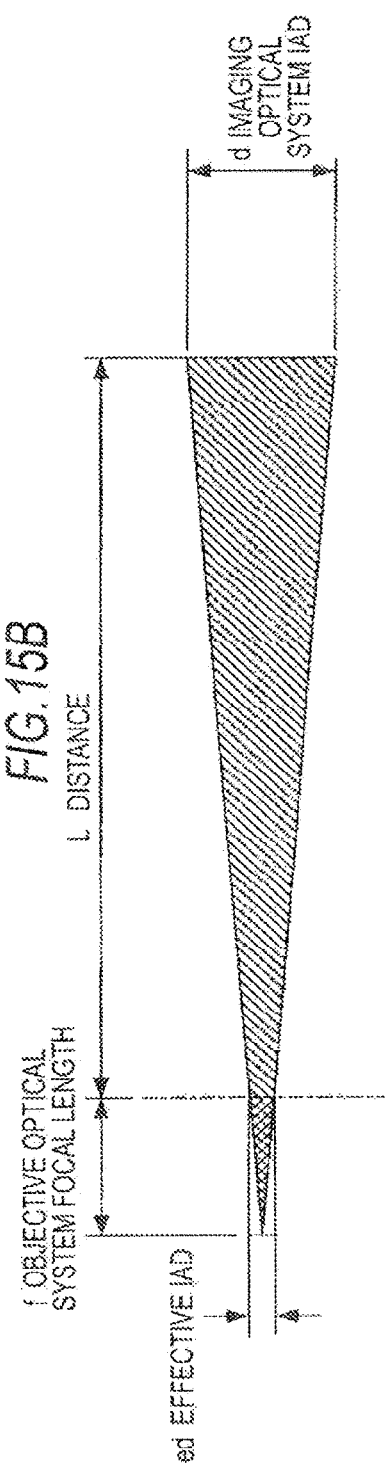

FIGS. 15A and 15B are diagrams for explanation of a calculation method of an effective IADed when the concave lens is used for the objective optical system 10α. In FIGS. 15A and 15B, the same signs are assigned to the parts corresponding to those in FIGS. 5A and 5B, and their detailed explanation will be omitted. FIG. 15A shows paths of beams in parallel to the optical axis A1 of beams from the subject S (not shown) toward the lens centers of the imaging optical systems 20a (20b). The paths in which the beams actually travel are shown by solid lines and apparent beams seen from view points of the lenses of the imaging optical systems 20a and 20b are shown by broken lines. Further, the beams in parallel to the optical axis A1 shown by the solid lines and the apparent beams shown by the broken lines collide with the objective optical system 10α, and then, intersect at two points. The distance between the two points is an effective IADed.

FIG. 15B extracts only a characteristic part necessary for obtainment of the effective IADed of the information shown in FIG. 15A. In the drawing, two triangles having similarity shapes to each other are shown. One is a shaded larger triangle having a bottom side of the imaging optical system IADd as the distance between the respective lenses of the imaging optical systems 20a, 20b and a height of (objective optical system focal length f+distance L). The other one is a hatched smaller triangle having a bottom side of the effective IADed and a height of the focal length f of the objective optical system 10α. These two triangles have similarity shapes to each other, and they are expressed by the following equation 4 because of their property.

Effective IADed: Imaging optical system
IADd=Objective optical system focal length $f$:
Distance $L$+Objective optical system focal length $f$ Further, since the focal length f when the concave lens is used is negative (f<0), $ed \times (L+(-f))=f \times d$, and $ed=|f/(L-f)| \times d$      Eq. (4)

is calculated.

That is, in both the case of using the convex lens and the case of using the concave lens for the lens of the objective optical system 10, the effective IADed may be calculated using the equation 4. Further, in both the case of using the convex lens and the case of using the concave lens for the lens of the objective optical system 10, by setting the focal length f of the objective optical system 10 and the distance L to satisfy the following equation 5, the effective IADed may be made shorter than the actual imaging optical system IADd.

$|f/(L-f)| \leq 1$      (Eq. 5)

In this manner, even when the concave lens is used for the lens of the objective optical system 10, the same advantage as that when the convex lens is used may be obtained. Further, when the concave lens is used, because the focal length f is negative compared to the case where the convex lens is used, the distance L necessary for realization of the same effective IADed for the same focal length |f| and the same imaging optical system IADd as those when the convex lens is used can be taken shorter. Therefore, the stereoscopic imaging apparatus 1α may be formed to be smaller.

The present disclosure contains subject matter related to that disclosed in Japanese Priority Patent Application JP 2010-251750 filed in the Japan Patent Office on Nov. 10, 2010, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An endoscope comprising:
   an objective optical system configured to image a subject as a real image or a virtual image;
   two separated imaging optical systems configured to form images from plural subject luminous fluxes output from different paths of the objective optical system again as parallax images; and
   two virtual effective pupils located a first distance and a second distance from the objective optical system and spaced apart from an optical axis of the objective optical system, wherein a distance between central points of the two virtual effective pupils is less than a distance separating optical axes of the imaging optical systems, wherein the luminous fluxes converge through the two virtual effective pupils.

2. The endoscope according to claim 1, wherein a focus point of each of the imaging optical systems is set to a predetermined position within a finite distance.

3. The endoscope according to claim 1, wherein the objective optical system and the imaging optical systems are placed so that their optical axes are located on a same plane.

4. The endoscope according to claim 1, wherein the objective optical system and the imaging optical systems are placed so that their optical axes are located on different planes.

5. The endoscope according to claim 1, wherein in the case where a focal length value when the objective optical system images the subject as the real image is positive and the focal length value when the objective optical system images the subject as the virtual image is negative, a focal distance (f) of the objective optical system and a distance (L) from a rear principal point of the objective optical system to a front principal point of the imaging optical systems is set to values that satisfy the following equation $|f/(L-f)|<1$.

6. The endoscope according to claim 1, wherein the two imaging optical systems include plural imagers.

7. The endoscope according to claim 1, wherein no lensing system is located between the objective optical system and the two imaging optical systems.

8. The endoscope according to claim 1, wherein the objective optical system comprises multiple lenses.

9. An imaging apparatus comprising:
   an objective optical system configured to image a subject as a real image or a virtual image; and
   two separated imaging optical systems configured to form images from plural subject luminous fluxes output from different paths of the objective optical system again as parallax images; and
   two virtual effective pupils located a first distance and a second distance from the objective optical system and spaced apart from an optical axis of the objective optical system, wherein a distance between central points of the two virtual effective pupils can be made less than a distance separating optical axes of the imaging optical systems, wherein the luminous fluxes converge through the two virtual effective pupils.

10. The imaging apparatus according to claim 9, wherein a focus point of each of the imaging optical system is set to a predetermined position within a finite distance.

11. The imaging apparatus according to claim 9, wherein the objective optical system and the imaging optical systems are placed so that their optical axes are located on a same plane.

12. The imaging apparatus according to claim 9, wherein the objective optical system and the imaging optical systems are placed so that their optical axes are located on different planes.

13. The imaging apparatus according to claim 9, wherein in the case where a focal length value when the objective optical system images the subject as the real image is positive and the focal length value when the objective optical system images the subject as the virtual image is negative, a focal distance (f) of the objective optical system and a distance (L) from a rear principal point of the objective optical system to a front principal point of the imaging optical system is set to values that satisfy the following equation $|f/(L-f)| \leq 1$.

14. The imaging apparatus according to claim 9, wherein the two imaging optical systems include plural imagers.

15. The imaging apparatus according to claim 9, wherein no lensing system is located between the objective optical system and the two imaging optical system.

16. The imaging apparatus according to claim 9, wherein a separation of the virtual effective pupils is different from a separation between optical axes of the imaging optical systems.

17. The imaging apparatus according to claim 9, wherein the objective optical system comprises multiple lenses.

* * * * *